United States Patent [19]

Habermeier

[11] 3,954,790

[45] May 4, 1976

[54] HALOGEN-SUBSTITUTED BENZIMIDAZOLONE COMPOUNDS

[75] Inventor: Jürgen Habermeier, Pfeffingen, Switzerland

[73] Assignee: Ciba-Geigy Corporation, Ardsley, N.Y.

[22] Filed: Nov. 5, 1974

[21] Appl. No.: 521,228

[30] Foreign Application Priority Data

Nov. 13, 1973 Switzerland............... 15953/73

[52] U.S. Cl................. 260/309.2; 260/45.8 N; 260/75 N
[51] Int. Cl.².................................. C07D 235/26
[58] Field of Search.................. 260/309.2

[56] References Cited
UNITED STATES PATENTS 3,024,166  3/1962  Kuna et al. ............. 260/309.2
3,207,604  9/1965  Rauch et al. ............ 260/309.2
3,843,674  10/1974 Porret ................. 260/309.2

OTHER PUBLICATIONS

Sawlewicz et al., Chem. Abst., 1964, Vol. 60, Col. 4129.

*Primary Examiner*—Natalie Trousof
*Attorney, Agent, or Firm*—Luther A. R. Hall

[57] ABSTRACT

New chlorinated and/or brominated N,N'-substituted benzimidazolones are obtained by reacting N,N'-substituted benzimidazolones with chlorine or bromine. The new chlorine-containing and/or bromine-containing benzimidazolone compounds are suitable for the production of heat-stable, flame-resistant polymers.

21 Claims, No Drawings

HALOGEN-SUBSTITUTED BENZIMIDAZOLONE COMPOUNDS

The present invention relates to new chlorine-substituted or bromine-substituted benzimidazolone compounds, a process for their manufacture and their use.

It is known that products having flame-retarding properties are obtained by incorporating organic halogen compounds in polymers. However, many organic halogen compounds have the disadvantage that they are insufficiently stable at elevated temperature and are therefore unsuitable for the manufacture of heat-stable plastics.

The preparation of benzimidazolone containing halogen has already been described repeatedly in the literature. Thus, for example, it is reported by H. Röchling et al. in "Zeitschrift für Naturforschung" 25 b, 954–960 (1970) that tetrachlorobenzimidazolone is obtained in a yield of 46% of theory by chlorinating benzimidazolone, long reaction times being also required and it being also necessary to react at high dilution.

Another method for the preparation of tetrachlorobenzimidazolone is described by D. E. Burton et al. in "Journal of Chemical Society" (C) 1968, on pages 1268 et seq. and consists in reacting tetrachloro-o-phenylenediamine, obtained via several reaction stages, in an excess of urea in the last stage.

It has now been found that heat-stable, chloro-substituted and/or bromo-substituted benzimidazolone compounds are obtained in a more economical manner and in better yields if certain N,N'-substituted benzimidazolone compounds are chlorinated or brominated in a known manner.

The present invention therefore relates to new chlorine-containing and/or bromine-containing benzimidazolone compounds of the formula I

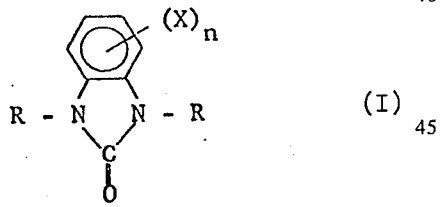

(I)

wherein X denotes chlorine and/or bromine, n denotes a number from 1 to 4 or from 2 to 4, and R denotes a radical of the formulae —CH$_2$—OH, —CH$_2$—CH$_2$—OH, —CH$_2$—CH—OH,    —CH$_2$—CH—OH,
       |                 |
       CH$_3$            C$_2$H$_5$

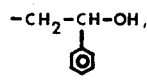

a = 3 or 4,        —CH$_2$—CH—CH$_2$—OH,
                          |
                          OH

CH$_2$—CH$_2$—CN    CH$_2$—CH$_2$—COOR$_2$,

—CH$_2$—COOR$_2$, wherein R$_2$ represents H or alkyl having 1–4 C atoms, —CH$_2$—CH$_2$—CH$_2$—NH$_2$ or —(CH$_2$)$_b$—X, b = 1–12.

In the formula I, X preferably denotes chlorine or bromine, n is equal to 4 and R denotes a radical of the formulae —CH$_2$—OH, —CH$_2$—CH$_2$—OH,

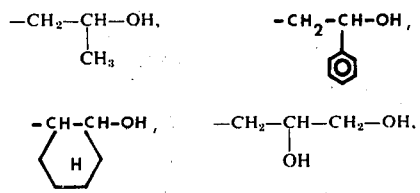

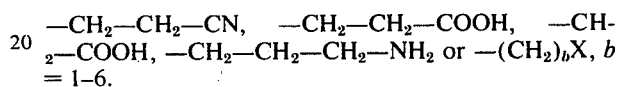

—CH$_2$—CH$_2$—CN, —CH$_2$—CH$_2$—COOH, —CH$_2$—COOH, —CH$_2$—CH$_2$—CH$_2$—NH$_2$ or —(CH$_2$)$_b$X, b = 1–6.

Particularly interesting compounds of the formula I are those wherein X denotes chlorine or bromine, n is equal to 4 and R denotes a radical of the formulae —CH$_2$—OH, —CH$_2$—CH$_2$—OH,

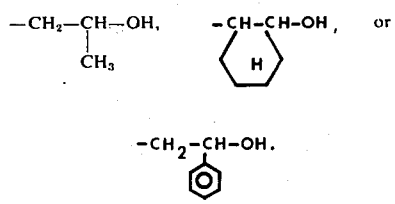

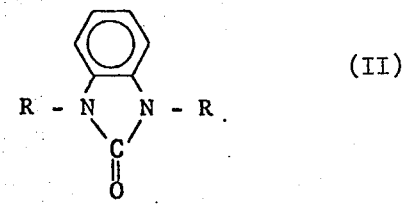

The new bromine-containing and chlorine-containing benzimidazolone compounds of the formula I are obtained by reacting 1 mol of a benzimidazolone compound of the formula II

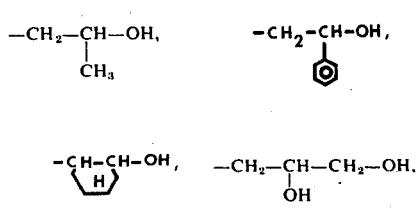

(II)

wherein R has the same meaning as in formula I, with n mols of bromine and/or chlorine.

In this process it is preferable to use benzimidazolone compounds of the formula II wherein R denotes a radical of the formulae —CH$_2$—OH, —CH$_2$—CH$_2$—OH,

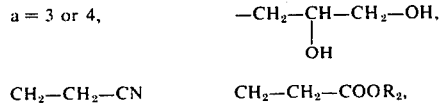

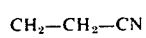

—$CH_2$—$CH_2$13 CN, —$CH_2$—$CH_2$—COOH, —$CH_2$—COOH, —$CH_2$—$CH_2$—$CH_2$—$NH_2$ or —$(CH_2)_bX$ $b$ = 1–6, and to react the latter with 4 mols of bromine or chlorine.

In a special embodiment, compounds of the formula II wherein R denotes a radical of the formulae —$CH_2$—OH, —$CH_2$—$CH_2$—OH,

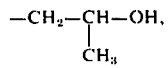 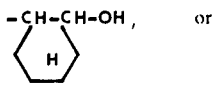 or

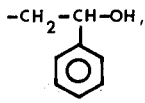

are used and the latter are reacted with 4 mols of bromine or chlorine.

This conversion reaction proceeds practically quantitatively in the absence of catalysts, if it is carried out in water and in the temperature range of 40° – 100°C, preferably 80° – 100°C. However, it is also possible to use mixtures of water and organic solvents. The ratio of water to starting substance employed is preferably chosen so that the relevant amount of the starting material just dissolves at 90° – 95°C.

The chlorine or bromine is added to this hot solution by being passed in or by dropwise addition, $n$ mols of the halogen being used per mol of the starting compound; it is preferable to use a slight molar excess of bromine or chlorine.

When preparing defined benzimidazolone derivatives containing bromine and chlorine, the bromination and chlorination are carried out successively. The desired products separate out from the hot, aqueous solution during the course of the reaction. After cooling, they can be separated off by filtration and can be dried. The substances produced in this way are pure enough for many applications. If higher demands are made on the degree of purity of the products obtained by the process according to the invention, these products can be recrystallised readily from organic solvents.

The following are examples of benzimidazolone compounds which can be used as starting compounds of the formula II for the process according to the invention: 1,3-di-(2-hydroxyethyl)-benzimidazolone, 1,3-di-(2-hydroxy-2-phenylethyl)-benzimidazolone, 1,3-di-(2-hydroxy-n-propyl)-benzimidazolone, 1,3-di-(2-hydroxy-n-butyl)-benzimidazolone, 1,3-di-(hydroxymethyl)-benzimidazolone, 1,3-di-(2-hydroxycyclohexyl)-benzimidazolone, 1,3-di-(2-hydroxycyclopentyl)-benzimidazolone, 1,3-di-(cyanoethyl)-benzimidazolone, 1,3-di-(carboxyethyl)-benzimidazolone, 1,3-di-(3-aminopropyl)-benzimidazolone, 1,3-di-(2-bromoethyl)-benzimidazolone, 1,3-di-(carboxymethyl)-benzimidazolone, 1,3-di-(2-bromoethyl)benzimidazolone and 1,3-di-(2,3-dihydroxypropyl)-benzimidazolone.

The starting compounds of the formula II are prepared by reacting benzimidazolone with compounds which produce the substituents R in their reactive form.

1,3-Di-(hydroxymethyl)-benzimidazolone is obtained, analogously to the process described in British Pat. No. 564,424, by a catalytic addition reaction of 2 mols of formaldehyde with 1 mol of benzimidazolone.

The other bis-hydroxyalkyl-substituted benzimidazolones can be obtained, analogously to the process described in U.S. Pat. No. 3,629,263, by an addition reaction of 2 mols of alkylene oxide, such as ethylene oxide, propylene oxide, butylene oxide, styrene oxide, cyclohexene oxide, cyclopentene oxide or glycerol glycide, preferably in the presence of a catalyst, with 1 mol of benzimidazolone.

1,3-Di-(Cyanoethyl)-benzimidazolone can be prepared conveniently in a known manner by cyanoethylation of benzimidazolone. From 1,3-di-(cyanoethyl)-benzimidazolone it is possible to obtain, in a known manner, on the one hand 1,3-di-(aminopropyl)-benzimidazolone by catalytic hydrogenation in the presence of ammonia, and, on the other hand, 1,3-di-(carboxyethyl)-benzimidazolone by hydrolysis in the presence of strong bases or mineral acids. The latter can also be prepared by reacting 1 mol of benzimidazolone with 2 mols of acrylic acid or 2 mols of $\beta$-halogenopropionic acid, particularly $\beta$-bromopropionic acid. 1,3-Di-(carboxymethyl)-benzimidazolone is obtained analogously by reacting 1 mol of benzimidazolone with 2 mols of chloroacetic acid.

The 1,3-di-($\omega$-chloroalkyl)-benzimidazolones or 1,3-di-($\omega$-bromoalkyl)-benzimidazolones can be obtained, analogously to the process described in U.S. Pat. No. 3,296,208, by reacting 1 mol of benzimidazolone with 2 mols of $\alpha$,107 -dihalogenoalkanes.

The chlorine-substituted and bromine-substituted benzimidazolone compounds according to the invention can also be prepared by reacting chlorine-substituted or bromine-substituted benzimidazolone which, however, as initially mentioned, is produced only in moderate yields by the process of Röchling, with 2 mols of formaldehyde, alkylene oxide, acrylonitrile, $\alpha$-or $\beta$-halogenocarboxylic acid or $\alpha,\omega$-dihalogenoalkane, analogously to the processes for preparing the starting compounds II.

The halogen-substituted benzimidazolone compounds according to the invention are interesting monomers which are suitable for the preparation of heat-stable, flame-resistant polymers. Thus, for example, the 1,3-di-(hydroxyalkyl)-4,5,6,7-tetrabromobenzimidazolones can be converted by means of polycarboxylic acids into polyesters which have flame-retarding properties and mechanical properties which are of great industrial value. In comparison, it is not possible, for example, to prepare polyesters from tetrabromobisphenol A diglycol ether, since decomposition reactions set in even during the polycondensation. The 1,3-di-(hydroxyalkyl)-4,5,6,7-tetrabromobenzimidazolones or 1,3-di-(hydroxyalkyl)-4,5,6,7-tetrachlorobenzimidazolones are also suitable for the preparation of polyurethanes or diglycidyl ethers. The 1,3-di-(chloroalkyl)-4,5,6,7-tetrachlorobenzimidazolones or 1,3-di-(chloroalkyl)-4,5,6,7-tetrabromobenzimidazolones are interesting additives for the manufacture of flame-resistant plastics. The 1,3-divinyl-4,5,6,7-tetrabromobenzimidazolones or 1,3-divinyl-4,5,6,7-tetrachlorobenzimidazolones, optionally mixed with other divinyl compounds, can be polymerised easily to give polymers having flame-retarding properties.

EXAMPLE 1

1,3-Di-(2-hydroxyethyl)-4,5,6,7-tetrabromobenzimidazolone a. 1,3-Di-(2-hydroxyethyl)-benzimidazolone

A solution of 269.4 g (6.12 mols) of ethylene oxide in 300 g of dimethylformamide is added dropwise to a solution of 402 g (3.0 mols) of benzimidazolone and 3 g of lithium chloride in 1,200 g of dimethylformamide at a temperature of 140° to 148°C (bath temperature: 145° to 150°C) over the course of 110 minutes. The reaction is complete after a reaction time of a further 40 minutes at 140°C to 145°C. The reaction mixture is concentrated to dryness in a rotary evaporator at 20 mm Hg and the residue obtained is subsequently dried at 90°C under 20 mm Hg. 645 g (96.8% of theory) of a yellow powder having a melting point of 145° to 158°C are obtained.

The crude product can be purified by recrystallisation in water in the ratio of 1:2; the pure substance is obtained in a 76.9% yield. The product melts at 161.2° to 163.4°C.

Elementary analysis:

| Found | Calculated |
|---|---|
| 59.56% C | 59.45% C |
| 6.42% H | 6.35% H |
| 12.59% N | 12.60% N |

The proton-magnetic resonance spectrum (H-NMR) is compatible with the following structure:

HO - CH$_2$ - CH$_2$ - N N - CH$_2$ - CH$_2$ - OH
\\C//
‖
O b. Bromination of (a)

333.3 g of 1,3-di-(2-hydroxyethyl)-benzimidazolone (1.5 mols) are stirred in a reaction flask with 3.5 liters of water at 90°C until a clear solution is formed. 1,198 g of bromine (7.5 mols) are then added dropwise with gentle stirring over the course of 30 minutes. A yellowish precipitate settles out at once. After the dropwise addition, the reaction mixture is stirred more vigorously for a further 4 – 5 hours, in order to achieve more thorough mixing, and the internal temperature is raised to 92° – 96°C.

The hydrogen bromide formed in the reaction and the excess bromine vapours are fixed by means of 5% strength sodium hydroxide solution in a washing tower filled with active charcoal.

The reaction mixture is subsequently cooled to 5° – 10°C and the product is isolated by filtration with suction. It is purified by being stirred with 5 liters of water and is again filtered off under strong suction. After being sucked dry, the product is dried in a vacuum cabinet at 100°C.

778.5 g (96.6% of the theoretical yield) of a practically colourless product melting at 266.2°C (Mettler "FP 51", heating rate 1°C/minute) are obtained.

100 g of the product are purified by recrystallisation from 300 ml of a dimethylformamide/isopropanol solvent mixture (mixing ratio 3:1). After drying at 150°C, 75.4 g of pure white needles are obtained, melting point 267.4°C.

Recrystallisation of 35 g of the crude product, melting at 266.2°C, from 150 ml of glycol gives very fine, colourless needles of melting point 267.5°C.

The elementary analysis (for $C_{11}H_{10}Br_4N_2O_3$) gives:

| Found | Calculated |
|---|---|
| 24.76% C | 24.57% C |
| 1.92% H | 1.87% H |
| 5.21% N | 5.21% N |
| 59.45% Br | 59.43% Br |

The H-NMR spectrum is in agreement with the following structure:

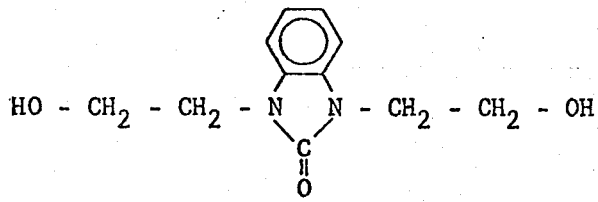

EXAMPLE 2

1,3-Di-(2-hydroxyethyl)-4,5,6,7-tetrachlorobenzimidazolone a. Chlorination of 1,3-di-(2-hydroxyethyl)-benzimidazolone 222.2 g of the benzimidazolone derivative prepared in Example (1a) are dissolved in 2 liters of water at 90°C. 425.4 g of chlorine gas (13.4 liters) are passed into this clear solution at 90° – 100°C over the course of 6 hours. The chlorine flow is checked by means of a rotameter flowmeter. A device for equalising the pressure is interposed between the chlorine cylinder and the rotameter. The stream of hydrogen chloride set free in the reaction is once more absorbed in a column charged with active charcoal through which 10% strength sodium hydroxide solution circulates.

The product begins to precipitate after about 1.5 hours of passing in chlorine gas. When the supply of chlorine gas is complete, a thick, colourless mash is formed. The reaction mixture is worked up as described in Example (1b).

333.5 g (92.6% of theoretical yield) of the crude tetrachloro compound are obtained in the form of colourless crystals of melting point 237.8°C.

The product can with advantage be recrystallised from a dioxane-ethylene glycol solvent mixture (mixing ratio (1:1). This gives colourless, fine, crystalline needles melting at 242°–244°C.

The NMR spectrum is virtually identical with that of the product prepared according to Example 1. This proves that the reaction has followed an analogous course and that the product has the structure given below.

Microanalysis (for $C_{11}H_{10}Cl_4N_2O_3$) gives:

| Found | Calculated |
| --- | --- |
| 36.65% C | 36.69% C |
| 2.76% H | 2.76% H |
| 7.80N % | 7.78% N |
| 39.34% Cl | 39.37% Cl |

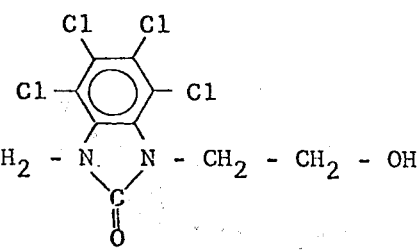

recrystallisation in water; its melting point then is 149° to 152°C.

Elementary analysis:

| Found: | Calculated: |
| --- | --- |
| 62.20% C | 62.38% C |
| 7.07% H | 7.25% H |
| 11.26% N | 11.19% N |

The H-NMR spectrum is in agreement with the following structure:

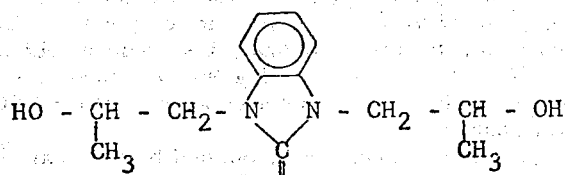

b. Chlorination of (a)

250.3 g of 1,3-di-(2-hydroxy-n-propyl)-benzimidazolone (1.0 mol) are reacted in 2 liters of water at 95°–100°C with 425.4 g of chlorine in accordance with the procedure described in in Example (2b).

Whilst maintaining the reaction conditions specified there, a flocculated crystalline mass is obtained after the completion of the reaction. The mixture is cooled, supernatant water is decanted off and the product is dissolved in 500 ml of dioxane and is precipitated from 7 liters of cold water. This gives colourless, fine crystals (367.2 g, corresponding to 94.6% of the theoretical yield) of melting point 138.8°C. A sample recrystallised from acetone melts at 158°C. The H-NMR spectrum is in agreement with the structure given below.

The elementary analysis (for $C_{13}H_{14}Cl_4N_2O_3$) gives:

| Found | Calculated |
| --- | --- |
| 39.85% C | 40.23% C |
| 3.63% H | 3.63% H |
| 7.20% N | 7.22% N |
| 36.25% Cl | 36.54% Cl |

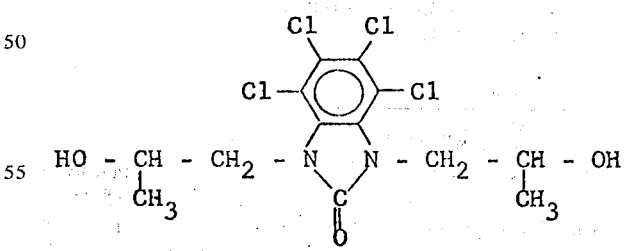

EXAMPLE 3

1,3-Di-(2-hydroxy-n-propyl)-4,5,6,7-tetrachlorobenzimidazolone a. 1,3-Di-(2-hydroxy-n-propyl)-benzimidazolone 61.0 g of propylene oxide are added dropwise to 67.0 g (0.5 mol) of benzimidazolone, 150 ml of dimethylformamide and 1.0 g of lithium chloride, over the course of 135 minutes at a temperature of 130°–140°C (bath temperature: 150°–162°C).

After 35 minutes, the reaction product is treated with 10 g of active charcoal and, after a further 13 minutes, it is filtered hot. The clear, brown filtrate is concentrated in a rotary evaporator at 90°C under a water-pump vacuum and the residue is subsequently dried at 90°C and $10^{-1}$ mm Hg to constant weight.

124.7 g (99.6% of theory) of a grey-brown, crystalline crude product are obtained, which is purified by

EXAMPLE 4

1,3-Di-(2-hydroxy-n-propyl)-4,5,6,7-tetrabromobenzimidazolone b. Bromination of 1,3-di-(2-hydroxy-n-propyl)-benzimidazolone 229.0 g (0.91 mol) of 1,3-di-(2-hydroxy-n-propyl)-benzimidazolone prepared according to Example (3a)

are reacted in 2.1 liters of water with 730.2 g (4.57 mols) of bromine, in accordance with Example (1b).

The product is worked up and purified as described in Example (3b). 418 g of a light yellow substance (81.3% of the theoretical yield) which melts at 151°C, are obtained. A sample recrystallised from acetone melts at 164.1°C. The NMR spectrum is in agreement with the structure given below.

Microanalysis (for $C_{13}H_{14}Br_4N_2O_3$) gives:

| Found | Calculated |
|---|---|
| 28.02% C | 27.59% C |
| 2.70% H | 2.49% H |
| 5.03% N | 4.95% N |
| 53.91% Br | 56.48% Br |

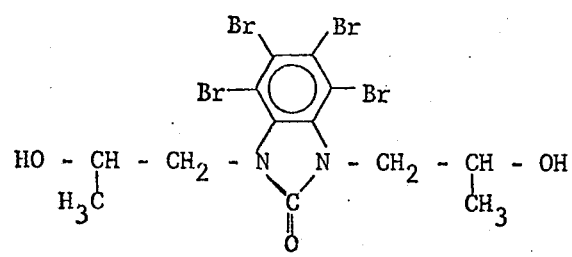

EXAMPLE 5

1,3-Di-(hydroxymethyl)-4,5,6,7-tetrabromobenzimidazolone a. 1,3-Di-(hydroxymethyl)-benzimidazolone 40 g (0.3 mol) of benzimidazolone, 0.5 g of borax and 63 g of 30% strength aqueous formaldehyde solution (0.63 mol) are adjusted to pH 8 with 1 N NaOH and are heated slowly. 10 ml of water are added after 7, 16, 44 and 54 minutes and the internal temperature is thus raised to 90°C over the course of 45 minutes. The mixture is allowed to react for a further 15 minutes at this temperature, a dark brown, clear solution being formed. The mixture is then cooled and the product which has crystallised out is filtered off and washed with water. The crystals are dried at 80°C/20 mm Hg, giving 56.4 g (96.7% of theoretical yield) of brownish crystals having a melting point of 157.4°–161°C.

Elementary analysis:

| Found | Calculated |
|---|---|
| 55.6% C | 55.7% C |
| 14.4% N | 14.4% N |

The H-NMR spectrum is compatible with the following structure:

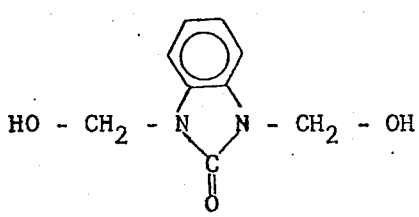

b. Bromination of (a)

58.2 g of the diol prepared according to (a) (0.3 mol) are dissolved in 350 ml of water at 90°C and 255.7 g of bromine (1.6 mols) are added dropwise with stirring over the course of 1 hour. The bromination is carried out in accordance with Example (1b). After the dropwise addition of the bromine, during which a granular, yellow precipitate is formed, the mixture is stirred at 90°C for a further 4 hours.

Working up is carried out in accordance with Example 1 to give, after drying the reaction product, 112 g (=73.3% of the theoretical yield) of colourless crystals, with a melting point >300°C. The NMR spectrum of a sample recrystallised from dioxane (Mp >300°C) shows that the new compound is in agreement with the following structure:

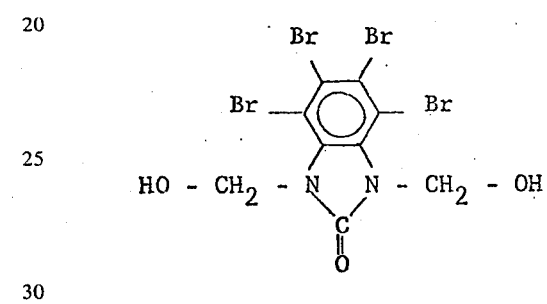

Bromine content:

| Found | Calculated |
|---|---|
| 62.81% | 62.68% |

EXAMPLE 6

1,3-Di-(cyanoethyl)-4,5,6,7-tetrabromobenzimidazolone a. 1,3-Di-(cyanoethyl)-benzimidazolone A mixture of 403.3 g of benzimidazolone (3 mols), 4.5 liters of dimethylformamide and 4.5 g of a 40% strength methanolic solution of benzyltrimethylammonium hydroxide is stirred at 90°C. 334.3 g of acrylonitrile (6.3 mols) are added dropwise to the clear solution over the course of 90 minutes. The addition reaction which now sets in is slightly exothermic, so that the heating bath is removed during the dropwise addition, in order to enable the temperature to be held at 90°C. The exothermic reaction is complete after the dropwise addition and the clear solution is stirred for a further hour at 95°C and for 2 hours at 115°C. The product is isolated by cooling the batch to 30°C, filtering it and completely concentrating the filtrate at 70°C. Thereafter, the product is dried at this temperature for 1 hour and is then dried at 0.5 mm Hg. 791.3 g are obtained of the crude product, which still contains a little dimethylformamide and which is in the form of light brown crystals melting at 164.5°C (Mettler "FP 51"; Heating rate 2°C per minute).

The crude product is recrystallised in the proportion of 1:5 from a solvent mixture consisting of dioxane and ethanol (2:1).

This gives 546.8 g (75.9% of the theoretical yield) of nearly colourless, glistening crystals, melting at 165.3°C.

b. Bromination of (a)

60.1 g of the product prepared according to (a) are brominated in accordance with Example 1. For this purpose the dinitrile is dissolved in 4.5 liters of water at 90°C and 319.5 g of bromine (2.0 mols) are added dropwise to this solution with stirring over the course of 3 hours. During the course thereof a light yellow precipitate is formed. The reaction solution is then stirred for a further 4 hours at 95°C. The product is isolated by cooling the solution to 5°C, filtering and washing the precipitate until free from acid.

The product is dried at 150°C/50 mm Hg, and 121.1 g (87.2% of theoretical yield) are obtained of a fine, light yellow powder melting at 231.2°C with decomposition.

A sample recrystallised from dimethylformamide/water (4:1) melts at 234°–236°C (Mettler "FP 51", 1°C/minute).

Elementary analysis gives a nitrogen content of 11.22% (calculated: 11.08%). The NMR spectrum is in agreement with the following structure:

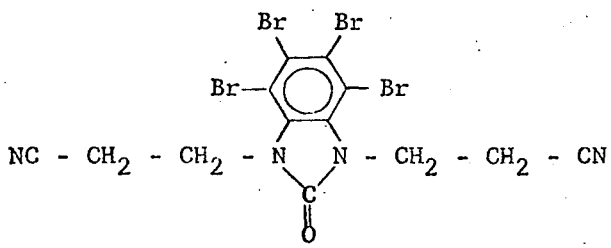

Microanalytical data for $C_{13}H_8Br_4N_4O$:

| Found | Calculated |
| --- | --- |
| 11.2% N | 11.1% N |
| 53.9% Br | 57.5% Br |

EXAMPLE 7

1,3-Di-(carboxyethyl)-4,5,6,7-tetrabromobenzimidazolone a. 1,3-Di-(carboxyethylbenzimidazolone)

60.06 g (0.25 mol) of the dinitrile prepared in accordance with Example (6a) and 340 ml of concentrated hydrochloric acid (approx. 4 mols) are stirred for 1 hour at room temperature, a clear, light brown solution being formed. Stirring is then continued for 5 hours at 75°–90°C. The solution is then completely concentrated, and the product is extracted, first with 500 ml of dioxane and then with 250 ml of dioxane. The combined dioxane solutions are cooled and the colourless crystals which separate out are filtered off and dried. This gives 60 g (86.3% of the theoretical yield) of bright crystals melting at 188.4°C. The crude product obtained in this way is purified by recrystallisation from water. The purified product melts at 188.9°C (Mettler "FP 51", 1°C/minute).

b. Bromination of (a)

56.47 g of the dicarboxylic acid prepared in accordance with (a) (0.22 mol) are dissolved in 550 ml of water at 90°C. 177.4 g of bromine (1.11 mols) are added dropwise with stirring over the course of 2 hours in accordance with Example 1, a pale precipitate being formed. After reacting further for 4 hours at 95°C, the reaction solution is cooled and worked up as described in Example 1b).

128.8 g (97.7% of the theoretical yield) are obtained of a colourless powder melting at 258.8°C. This is purified by recrystallisation from dioxane/water (3:1). The product purified in this way melts at 275.1°C.

Elementary analysis (for $C_{13}H_{10}Br_4N_2O_5$): gives:

| Found | Calculated |
| --- | --- |
| 26.32% C | 26.29% C |
| 1.93% H | 1.69% H |
| 52.05% Br | 53.83% Br |
| 4.94% N | 4.72% N |

The H-NMR spectrum is in agreement with the following structure:

HOOC - CH$_2$ - CH$_2$ - N\N - CH$_2$ - CH$_2$ - COOH (with 4,5,6,7-tetrabromobenzimidazolone ring, C=O)

EXAMPLE 8

1,3-Di-(2,3-dihydroxypropyl)-4,5,6,7-tetrabromobenzimidazolone a. 1,3-Di-(2,3-dihydroxypropyl)-benzimidazolone 1.5 mols of benzimidazolone (201.2 g) are dissolved in 1.5 liters of N,N-dimethylacetamide at 120°C and 2.5 g of lithium chloride are added. 244.2 g (3.3 mols) of glycerol glycide (glycidol) are added dropwise over the course of 2 hours to this solution. The solution is then stirred for a further 5 hours at 135°C. After bringing the solution to room temperature, it is filtered and completely concentrated. The residue is dried for a further 5 hours at 95°C under 0.8 mm Hg. This gives 448 g of a brownish, very viscous liquid (theoretical yield: 423.5 g) which is the crude product still contaminated with a little dimethylacetamide.

b. Bromination of (a)

The whole crude product obtained in accordance with (a) (approx. 1.5 mols) is dissolved in 3.5 liters of water at 90°C and 1,118 g of bromine (7.0 mols) are added dropwise over the course of 2½ hours. An oily-crystalline precipitate is produced. Stirring is continued for a further 4 hours at 95°C and the reaction solution is then cooled to room temperature. The water is decanted off from the crystals which separate out. As the mash of crystals is not filterable, it is dissolved in 2 liters of dioxane/acetone (1:1) and occluded hydrogen bromide is neutralised with sodium bicarbonate. The product is filtered, the filtrate is completely concentrated and the residue is dried under 0.5 mm Hg at 120°C for 6 hours.

This gives 796 g (88.8% of the theoretical yield) of the crude product, which still contains about 4% of impurities in the form of sodium bromide. The H-NMR spectrum shows that the product obtained has the following structure:

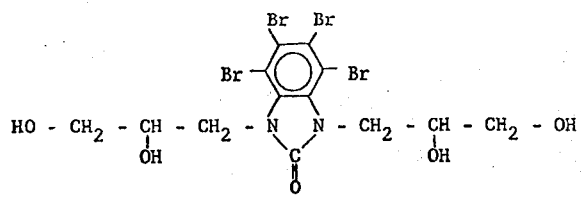

The crude product can be purified by reprecipitation from acetone/ether and subsequent recrystallisation from absolute ethanol. The product obtained in this way melts at 190°–193°C.

Elementary analysis gives the following values for $C_{13}H_{14}Br_4N_2O_5$:

| Found | Calculated |
|---|---|
| 54.2% Br | 53.5% Br |
| 4.4% N | 4.7% N |

EXAMPLE 9

1,3-Di-(2-hydroxyethyl)-4,7-dichloro-5,6-dibromobenzimidazolone a. Preparation of 1,3-di-(2-hydroxyethyl)-5,6-dibromobenzimidazolone 333.3 g (1.5 mols) of 1,3-di-(2-hydroxyethyl)-benzimidazolone in 3,700 ml of water are heated to 95°C with stirring. 511.4 g (3.2 mols) of bromine are added dropwise to this clear solution over the course of 70 minutes and a yellowish precipitate gradually separates out. After the dropwise addition, the reaction solution is stirred for a further 5 hours at 90°C, cooled to 10°C and filtered and the precipitate is washed free from acid by means of a large quantity of water. It is then dried to constant weight at 100°C/20 mm Hg.

This gives 537.7 g (94.3% of the theoretical yield) of colourless crystals melting at 189°C. They can be purified further by recrystallisation from a dioxane/ethylene glycol mixture (1:3). The colourless crystals melt at 195.7°C (Mettler "FP 51"; heating rate 1°C/minute).

Elementary analysis for $C_{11}H_{12}N_2Br_2O_3$ gives:

| Found | Calculated | (M = 380.036) |
|---|---|---|
| 34.70% C | 34.76% C | |
| 3.10% H | 3.18% H | |
| 7.40% N | 7.37% N | |
| 42.00% Br | 42.05% Br | |

According to a thin layer chromatogram (migrating agent cyclohexane: ethyl acetate: acetic acid: 30 : 50 : 20), the crystals consist of a homogeneous substance.

The NMR spectrum ($^{13}C$ satellites: 2 singlets) shows that only a symmetrical compound without ortho-coupling can be present, so that the compound has the following structure:

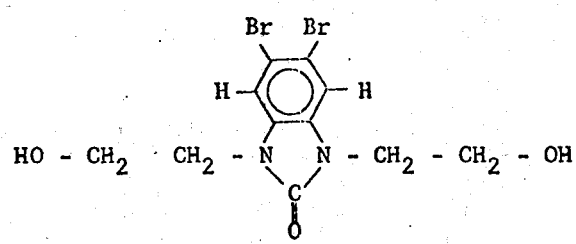

b. Chlorination of (a)

25 g (0.06578 mol) of the dibromo compound prepared in accordance with (a) are dissolved in 5 liters of water at 95°C. 6 liters of chlorine gas (0.263 mol) are passed in, with stirring, over the course of about 90 minutes, a colourless precipitate separating out. The reaction solution is then stirred for a further 4 hours at 90°C, cooled to 10°C and filtered and the precipitate is washed free from acid. After drying, 24.1 g (81.4% of the theoretical yield) are obtained of colourless crystals melting at 271.7°C (Mettler "FP 51"; heating rate 1°C/minute).

The melting point of a sample recrystallised from dioxane/ethylene glycol is 276°– 278°C.

Elementary analysis gives the following results for the crude product ($C_{11}H_{10}Cl_2Br_2N_2O_3$) (M = 448.9):

| Found | Calculated |
|---|---|
| 29.7% C | 29.43% C |
| 2.2% H | 2.24% H |
| 6.3% N | 6.24% N |
| 15.8% Cl | 15.79% Cl |
| 33.5% Br | 35.59% Br |

On the basis of the above elementary analytical results and according to NMR spectra, the new diol has the following structure:

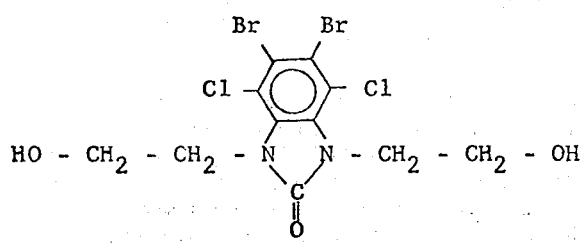

EXAMPLE 10

1,3-Di-(2-hydroxyethyl)-4,5,6,7-tetrabromobenzimidazolone 44.96 g (0.1 mol) of 4,5,6,7-tetrabromobenzimidazolone are stirred with 250 ml of dimethylacetamide and 2.5 g of lithium chloride. A solution of 13.2 g of ethylene oxide (0.3 mol) in 100 ml of dimethylacetamide is added to this mixture at room temperature. The mixture is stirred slowly and heated to 80°C over the course of 2.5 hours. It is then stirred for a further 2 hours at 100°C. During the course of the reaction the starting material dissolves completely.

Working up is carried out by filtering the cooled solution and concentrating the filtrate completely at 70°– 90°C. The residue is then dried to constant weight at 90°C under 0.2 mm Hg.

This gives 58.2 g of a light brown, solid substance (theory = 53.8 g), which is purified by recrystallisation from ethylene glycol.

The colourless needle-shaped crystals obtained in this way melt at 265°C. The product is identical with the product prepared in accordance with Example 1.

EXAMPLE 11

Preparation of 1,3-di-(2-hydroxyethyl)-5,6-dichlorobenzimidazolone

A solution of 222.2 g of 1,3-di-(2-hydroxyethyl)-benzimidazolone (1 mol) in 2.5 liters of water is stirred at 90°C. 2.0 g of iodine are added as catalyst and 184 g of chlorine are passed in from a cylinder (58.24 liters $\stackrel{\Delta}{=}$ 2.6 mols) over the course of 5 hours. The stream of chlorine is checked via a rotameter. Towards the end of the introduction of the chlorine, colourless crystals precipitate from the hot solution (90°–95°C). After the addition of chlorine is completed, the reaction solution is stirred for a further 3 hours at 90°C and is then cooled to 5°C with stirring and the product is isolated by filtration under suction. The precipitate is washed free from acid by means of water at 5°C and is dried to constant weight in a vacuum cabinet at 110°C.

The mother liquor is not washed up further; however, it still contains a proportion of the desired product.

The resulting crude product is obtained in the form of 190 g of a colourless crystalline powder (65.2% of theory); it melts at 175°– 177°C.

This crude product gives the following analytical values for $C_{11}H_{12}Cl_2N_2O_3$:

| Found | Calculated |
|---|---|
| 4.3% H | 4.2% H |
| 9.7% N | 9.6% N |
| 23.0% Cl | 24.3% Cl |

This crude product can be purified by recrystallisation from dioxane, which, however, is not necessary for the further reaction in accordance with Example 12 which follows.

The NMR spectrum ($^{13}C$ satellite: 2 singlets) shows that the following structure is present:

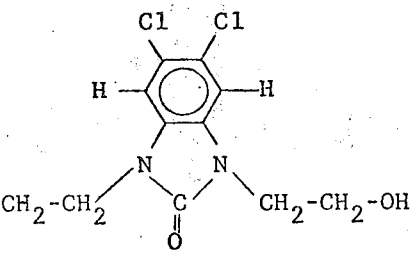

EXAMPLE 12

1,3-Di-(2-hydroxyethyl)-4,7-dibromo-5,6-dichlorobenzimidazolone 50 g of the crude dichloro compound prepared in accordance with Example 11 (0.17 mol) are dissolved in 5.5 liters of water at 95°C. 82.3 g (26.2 ml) of bromine (0.515 mol) are added dropwise to this solution over the course of 1 hour, colourless crystals beginning to precipitate. The reaction solution is then stirred for a further 4 hours at 95°C and is cooled to 5°C, and the crystals are isolated by filtration under suction and are washed free from acid by means of water.

After drying at 120°C, the desired crude product having the melting point 218°– 220°C is obtained quantitatively.

Recrystallisation in the proportion of 1 : 3 from ethylene glycol/dioxane (1 : 1) gives 56 g (73.4% of theory) of colourless crystals melting at 224°– 225°C.

Elementary analysis of $C_{11}H_{10}Br_2Cl_2N_2O_3$ gives:

| Found | Calculated |
|---|---|
| 29.50% C | 29.43% C |
| 2.20% H | 2.24% H |
| 6.20% N | 6.24% N |
| 35.20% Br | 35.60% Br |

-continued

| Found | Calculated |
|---|---|
| 15.70% Cl | 15.75% Cl |

The new product has the following structure:

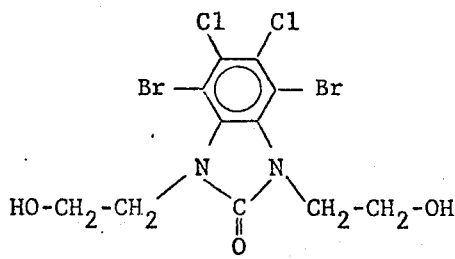

This product can be distinguished easily, by means of the greatly differing melting points, from the isomeric diol prepared in accordance with Example (9b):

4,7-Dibromo-5,6-dichloro derivative (Example 12): melting point = 224°– 225°C.

4,7-Dichloro-5,6-dibromo derivative (Example 9b): melting point = 276°– 278°C.

EXAMPLE 13

1,3-Di-(2-hydroxyethyl)-4,5,6-tribromobenzimidazolone 333.3 g of 1,3-di-(2-hydroxyethyl)-benzimidazolone (1.5 mols) are reacted, in 3.5 liters of water at 90°–95°C, with 838.98 g of bromine (5.25 mols) in accordance with Example (1b). After carrying out the reaction and working up in accordance with Example (1b), 633.3 g (92% of theory) are obtained of a colourless, crystalline, crude product melting at 201°–204°C.

This product is purified by recrystallising twice from 1 : 1 glycol-dioxane. This gives 562.4 g of a colourless powder melting at 207°– 208°C. According to thin layer chromatography the product is homogeneous.

Elementary analysis for $C_{11}H_{11}Br_3N_2O_3$ gives:

| Found | Calculated |
|---|---|
| 28.70% C | 28.79% C |
| 2.40% H | 2.41% H |
| 6.20% N | 6.10% N |
| 52.90% Br | 52.2% Br |

The NMR spectrum ($^{13}C$ satellites) shows agreement with the following structure:

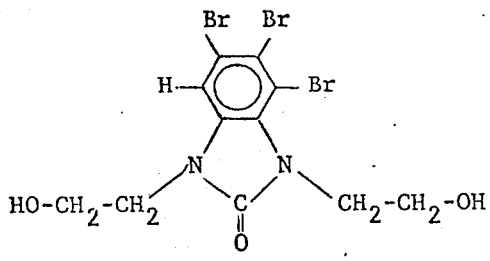

EXAMPLE 14

1,3-Di-(2-hydroxy-2-phenylethyl)-4,5,6,7-tetrabromobenzimidazolone 374.4 g of 1,3-di-(2-hydroxy-2-phenylethyl)-benzimidazolone (1.0 mol) are stirred into 4 liters of water at 93°– 95°C, the greater part of the product dissolving. 958.8 g of bromine (6.0 mols) are added dropwise to this suspension over the course of 6 hours. The reaction solution is then stirred further overnight at 92°– 95°C and is cooled to room temperature, 1 liter of ice water is added and the precipitated product is isolated by filtration under suction. This gives 527.3 g (76.4% of theory) of a pale yellow powder melting at 121°–123°C.

Elementary analysis for $C_{23}H_{13}Br_4N_2O_3$ gives:

| Found | Calculated |
|---|---|
| 39.0% C | 40.0% C |
| 2.5% H | 2.6% H |
| 47.3% Br | 46.3% Br |

The product contains traces of a hexabrominated compound which is formed from the tetrabrominated product by reaction of further bromine with the phenyl substituents.

The product prepared above essentially consists of:

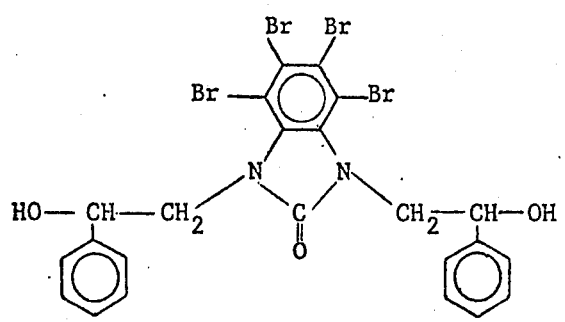

EXAMPLE 15

1,3-Di-(2-hydroxycyclohexyl)-5,6-dibromobenzimidazolone

A solution of 20 g of 1,3-di-(2-hydroxycyclohexyl)-benzimidazolone (0.06 mol) in 2 liters of dioxane-water (1 : 1) is stirred at 85°– 90°C and 20 ml of bromine are added dropwise over the course of 1.5 hours and the reaction solution is subsequently stirred overnight at 90°C. It is cooled to room temperature and stirred into 2 liters of ice water. The product is isolated by filtration under suction and the filter cake is recrystallised, while still moist, from ethanol.

Without working up the mother liquor, 11.3 g of colourless crystals (30% of theory) melting at 150°–152°C are obtained.

Elementary analysis for $C_{19}H_{24}Br_2N_2O_3$ gives:

| Found | Calculated |
|---|---|
| 5.45% N | 5.73% N |
| 32.87% Br | 32.73% Br |

The ¹H-NMR spectrum is in agreement with the following formula:

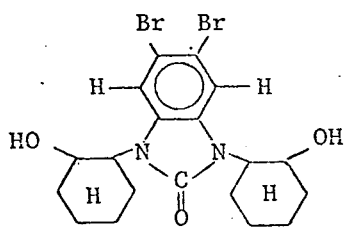

EXAMPLE 16

1,3-Di-(γ-aminopropyl)-4,5,6,7-tetrabromobenzimidazolone 225 g of 1,3-di-(γ-aminopropyl)-benzimidazolone (0.906 mol) are dissolved in 1,350 ml of water at 90°C. 796.4 g of bromine (4.98 mols) are added dropwise with stirring over the course of 2 hours. The reaction solution is then stirred for a further 6 hours at 95°C. After the dropwise addition an oily precipitate separates out. After cooling to room temperature, the aqueous phase is decanted off, the product is dissolved in hot water and the solution is neutralised with 20% strength sodium hydroxide solution (liberating the diamine from the di-(hydrobromide) formed). The precipitated material is isolated and dried at 120°C under a vacuum. The desired diamine is obtained in a 95% yield in the form of a pale ochrecoloured powder. The product melts with decomposition at ≈ 240°C.

Elementary analysis for $C_{13}H_{16}Br_4N_4O$ gives:

| Found | Calculated |
|---|---|
| 56.83% Br | 56.68% Br |
| 2.80% H | 2.86% H |

The product obtained corresponds to the following formula:

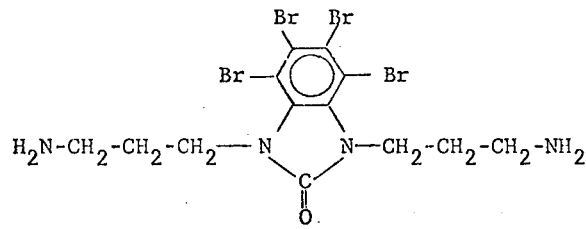

EXAMPLE 17

1,3-Di-(β-carboxyethyl)-4,5,6,7-tetrabromobenzimidazolone from 1,3-di-(cyanoethyl)-benzimidazolone 240.2 g of di-(β-cyanoethyl)-benzimidazolone (1.0 mol) are dissolved in 1.5 liters of 37% strength hydrochloric acid and 1 liter of water, and the mixture is stirred for 5 hours at 95°C. 210 ml of bromine (770 g) are then added dropwise over the course of 5 hours. Stirring is then continued for a further 5 hours at 95°C. The solution is cooled to 60°C, 1 liter of water is added and the precipitate produced is filtered off with suction while still warm. The residue on the filter is washed with 3 liters of hot water. The product is recrystallised, while still moist, from dioxane/water (2 : 1). This gives 392 g (65.9% of theory) of colourless crystals melting at 270°– 273°C. By further crystallisation it is possible to obtain a very pure product which corresponds to the product described in Example 7.

EXAMPLE 18

1,3-Di-(carboxymethyl)-4,5,6,7-tetrabromobenzimidazolone 17.4 g of 1,3-di-(methoxycarbonylmethyl)-benzimidazolone (0.05 mol) are dissolved in 75 ml of glacial acetic acid at 95°C and 26 ml of bromine (0.5 mol) are added dropwise over the course of 2 hours. The reaction is catalysed by means of 2 g of iodine. The solution is stirred for a further 6 hours at 95°C and cooled to room temperature, and the precipitate is filtered off and suspended in 2 liters of ice water. The precipitate which is obtained by filtration is dried at 120°C in a vacuum cabinet and 28.5 g of light brown crystals are obtained. Purification is carried out by recrystallisation from dioxane/water. After drying, 26 g of the crystalline compound (91.9% of theory) are obtained, melting above 300°C.

Elementary analysis for $C_{11}H_6Br_4N_2O_5$ gives:

| Found | Calculated |
|---|---|
| 55.00% Br | 56.48% Br |
| 1.09% H | 1.06% H |

The ¹H-NMR spectrum is in agreement with the structure which follows. It shows, above all, the absence of aromatic protons and of methyl ester groups.

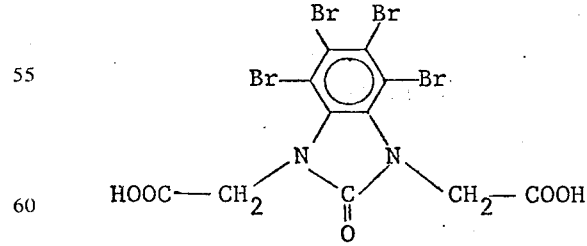

EXAMPLE 19

1,3-Di-(2-chloroethyl)-5,6,-dibromobenzimidazolone 0.1 mol of 1,3-di-(2-chloroethyl)-benzimidazolone (25.91 g) are dissolved in 3.5 liters of water at 95°C. 0.5 g of iodine are added as catalyst and 111.9 g of bromine (0.7 mol) are then added dropwise over the course of 2 hours. The solution is then stirred for a further 5 hours at 95°C. It is cooled to room temperature, 500 ml of ice water are added and the colourless crystals are filtered off. This crude product is recrystallised from dioxane.

34.2 g are obtained of colourless crystals (82.2% of theory) melting at 207°– 209°C.

Elementary analysis for $C_{11}H_{10}Br_2Cl_2N_2O$ gives:

| Found | Calculated |
|---|---|
| 31.20% C | 31.68% C |
| 6.60% N | 6.70% N |
| 39.03% Br | 38.33% Br |
| 16.93% Cl | 17.01% Cl |

The product obtained corresponds to the following formula:

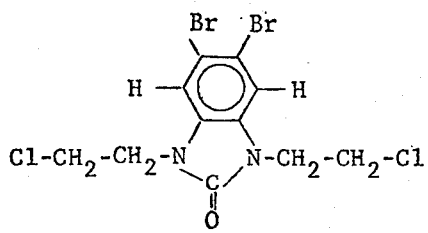

APPLICATION EXAMPLES

Example A (A copolyester containing approx. 20 percent by weight of bromine)

The following mixture is subjected to a polycondensation:
- 48.5 g of dimethyl terephthalate (0.25 mol),
- 45.1 g of 1,4-butanediol (0.5 mol),
- 26.9 g of diol according to Example 1 (0.05 mol) and
- 0.1 g of tetraisopropyl ortho-titanate, the following reaction conditions being applied:
- 2 hours/145 → 170°C/$N_2$/normal pressure,
- + 2 hours/170 → 220°C/$N_2$/normal pressure,
- + 1 hour /220 → 240°C/$N_2$/760 mm Hg → 20 mm Hg,
- + 1 hour /240°C/$N_2$/20 mm Hg → 0.2 mm Hg.

After the completion of the reaction, the polyester melt obtained in this way is poured out onto a metal sheet under nitrogen. This gives 65 g of a copolyester which at first is as clear as glass and is found to be partly crystalline on heat-treatment. This copolyester is flame-retarding. A sheet held in a flame is extinguished as soon as it is taken out of the flame. The polyester also has the following properties.

Composition from micro-analysis (for $n \times C_{67}H_{60}N_2Br_4O_{21}$):

| Found | Calculated |
|---|---|
| 52.2% C | 51.96% C |
| 4.1% H | 3.90% H |
| 1.9% N | 1.81% N |
| 20.5% Br | 20.64% Br |

| | |
|---|---|
| Relative viscosity (1% strength solution measured at 30.0°C in 1:1 phenol/tetrachloroethane) | 1.73 |
| Tg (glass transition temperature) in the as-delivered condition | 67 – 79°C |
| Tg after heat-treatment | 77 – 95°C |
| Fusion temperature (Tf) | 185°C |
| Softening point (by Kofler's method) | 182°C |
| Decomposition temperature | 309°C |

In comparison, pure polybutylene terephthalate is readily inflammable and has Tg = 24°C, and Tf = 220°C. The polyester prepared using the diol according to the invention has, therefore, additionally a higher glass transition temperature and also better processing properties.

Example B

Preparation of 1,3-di-(2-chloroethyl)-4,5,6,7-tetrabromobenzimidazolone from 1,3-di-(2-hydroxyethyl)-4,5,6,7-tetrabromobenzimidazolone 0.5 mol of the tetrabrominated diol prepared in accordance with Example (1b) is stirred at 95° – 100°C with 1.8 liters of dioxane and 1 ml of pyridine. 148.6 g of thionyl chloride (1.25 mols) are added dropwise over the course of 2 hours. The initial suspension becomes converted into a clear, light brown solution. It is then stirred for a further 5 hours under the conditions mentioned. The reaction solution is then cooled to room temperature and allowed to stand overnight, and the precipitated substance is isolated by filtration. 223.6 g are obtained and a further 54.8 g of the substance can be isolated from the mother liquor. Total yield: 278.4 g (corresponding to 96.9% of theory). The substance is purified by recrystallisation from dioxane, colourless crystals of melting point 194° – 195°C being obtained.

Elementary analysis for $C_{11}H_8Br_4Cl_2N_2O$ gives:

| Found | Calculated |
|---|---|
| 23.03% C | 22.99% C |
| 1.50% H | 1.40% H |
| 4.90% N | 4.87% N |
| 54.60% Br | 55.61% Br |
| 12.10% Cl | 12.34% Cl |

The new substance of the following formula can be used as a flame-retarding additive.

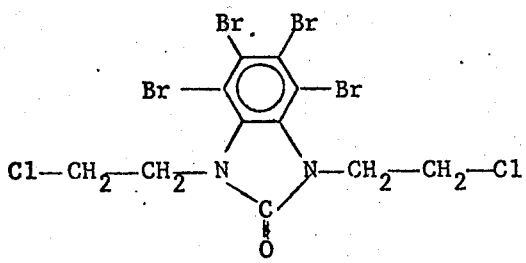

Example C

Preparation of 1,3-di-(2-chloroethyl)-4,5,6,7-tetrachlorobenzimidazolone from 1,3-di-(2-hydroxyethyl)-4,5,6,7-tetrachlorobenzimidazolone 1.0 mol of the tetrachlorinated diol prepared in accordance with Example (2a) (360 g) in 3.6 liters of dioxane containing 2 ml of pyridine is reacted, in accordance with Example (B), with 2.5 mols (297.2 g) of thionyl chloride. The reaction is carried out and the product is worked up and isolated as described in Example (B).

This gives 220.8 g (55.6% of theory) of pale ochrecoloured crystals melting at 156° – 158°C.

Elementary analysis for $C_{11}H_8Cl_6N_2O$ gives:

| Found | Calculated |
| --- | --- |
| 33.70% C | 33.29% C |
| 2.00% H | 2.03% H |
| 7.20% N | 7.06% N |
| 52.85% Cl | 53.52% Cl |

The new hexachloro compound, which is suitable as a flame-retarding additive for plastics, corresponds to the following structure:

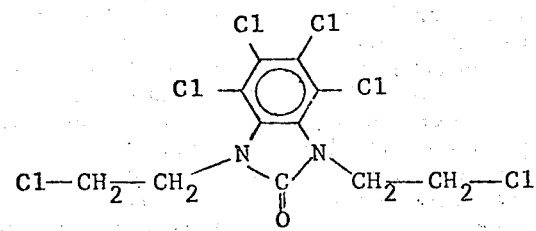

Example D

Dehydrochlorination of 1,3-di-(2-chloroethyl)-4,5,6,7-tetrachlorobenzimidazolone 39.7 g (0.1 mol) of 1,3-di-(2-chloroethyl)-4,5,6,7-tetrachlorobenzimidazolone (prepared by chlorination of 1,3-di-(2-chloroethyl)-benzimidazolone or in accordance with Application Example (C) are suspended in 200 ml of dioxane at 20°C. 22.5 g (0.2 mol) of potassium tertiary-butylate are added in portions to this suspension over the course of 10 minutes. In the course thereof the temperature rises to 30°C. The exothermic reaction is held in check by means of ice/water cooling. The suspension is then stirred for a further 2 hours at 20°C and filtered and the clear, pale yellow filtrate is concentrated to dryness.

This gives 32.4 g (100% of theory) of a light yellow powder melting at 135° – 140°C. It is purified by recrystallisation from tetrahydrofurane. Pale yellow crystals melting at 162° – 163.5°C are obtained.

Elementary analysis for $C_{11}H_8Cl_4N_2O$ gives:

| Found | Calculated |
| --- | --- |
| 43.70% Cl | 43.77% Cl |

The $^1$H-NMR spectrum is in agreement with the structure which follows. The substance can be polymerised easily, optionally mixed with other divinyl compounds.

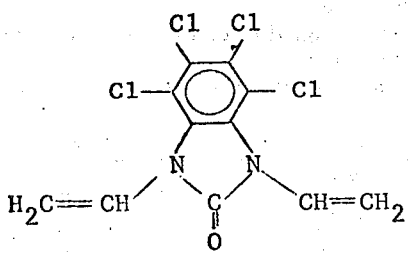

Example E

Diglycidylation of 1,3-di-(2-carboxyethyl)-4,5,6,7-tetrabromobenzimidazolone 178.6 g (0.3 mol) of the tetrabrominated dicarboxylic acid, prepared in accordance with Example 7 or Example 17, are stirred with 4 liters of epichlorohydrin at 111°-113°C under the catalytic influence of 20 ml of 50% strength aqueous tetramethylammonium chloride solution. A clear solution is formed after about ½ minute. After 1 hour, a circulatory distillation is set going, by the application of a vacuum, in such a way that, at a bath temperature of 165°C and a reaction temperature of 59°-61°C and with vigorous stirring, there is the greatest possible flow of epichlorohydrin through the circulatory apparatus. 57.6 g of 50% strength aqueous sodium hydroxide solution are then added dropwise over the course of 2 hours and the water present in the reaction mixture is removed by being circulated and separated off. After the dropwise addition of the alkali, distillation is continued for a further 30 minutes, the mixture is then cooled to 50°C, the vacuum is released, 20 g of active charcoal and 10 g of a filter aid are added and the sodium chloride formed in the reaction is filtered off. The epichlorohydrin solution is twice washed with 200 ml of water and the organic phase is then concentrated at 60°C on a rotary evaporator and the residue is subsequently dried to constant weight at 60°C/0.2 mm Hg.

This gives 226 g of a colourless, somewhat sticky crystalline mass (theory = 212 g), the epoxide content of which is 2.90 equivalents/kg (theory = 2.83 equivalents/kg). The compound is obtained in the form of colourless crystals of melting point 196°-198°C by recrystallisation from dioxane/ethyl acetate (4:1).

The new diglycidyl compound, the structure of which corresponds to the formula indicated below, is a valuable constituent in flame-retarding epoxide resin formulations.

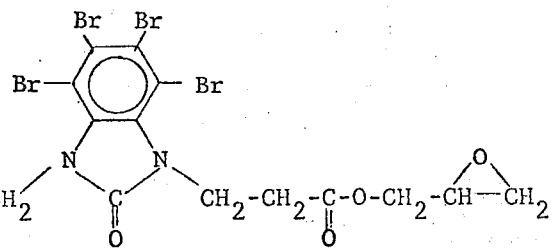

What we claim is:
1. A benzimidazolone compound of the formula I

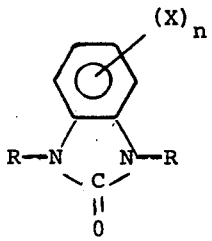

wherein X independently denotes chlorine or bromine, n denotes a number from 2 to 4, and R denotes a radical selected from the group consisting of —CH₂—OH, —CH₂—CH₂—OH,

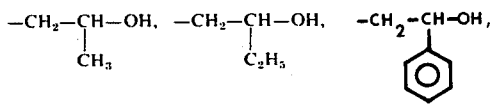

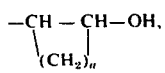

$a = 3$ or 4, —CH₂—CH—CH₂OH, —CH₂—CH₂—CN, —CH₂—CH₂—COOR₂, —CH₂—COOR₂, R₂ representing H or alkyl having 1–4 C atoms, —CH₂CH₂—CH₂—NH₂ and —(CH₂)$_b$—X, $b = 1$–12.

2. A benzimidazolone according to claim 1, wherein, in the formula I, X denotes chlorine or bromine, n is equal to 4, and R denotes a radical selected from the group consisting of —CH₂—OH, —CH₂—CH₂—OH,

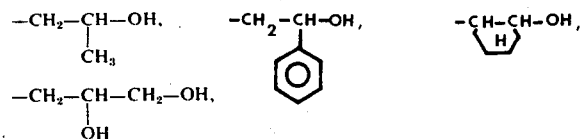

—CH₂—CH₂—CN, —CH₂—CH₂—COOH, —CH₂—COOH, —CH₂—CH₂—CH₂—NH₂ and —(CH₂)$_b$X, $b = 1$–6.

3. A benzimidazolone compound according to claim 1, wherein, in the formula I, X denotes chlorine or bromine, n is equal to 4, and R denotes a radical selected from the group consisting of —CH₂—OH, —C₂—CH₂—OH,

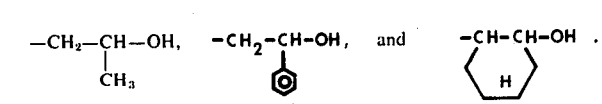

4. A compound as claimed in claim 1 which is 1,3-di-(2-hydroxyethyl)-4,5,6,7-tetrabromobenzimidazolone.
5. A compound as claimed in claim 1 which is 1,3-di-(2-hydroxyethyl)-4,5,6,7-tetrachlorobenzimidazolone.
6. A compound as claimed in claim 1 which is 1,3-di-(2-hydroxy-n-propyl)-4,5,6,7-tetrachlorobenzimidazolone.
7. A compound as claimed in claim 1 which is 1,3-di-(2-hydroxy-n-propyl)-4,5,6,7-tetrabromobenzimidazolone.
8. A compound as claimed in claim 1 which is 1,3-di-(hydroxymethyl)-4,5,6,7-tetrabromobenzimidazolone.
9. A compound as claimed in claim 1 which is 1,3-di-(cyanoethyl)-4,5,6,7-tetrabromobenzimidazolone.
10. A compound as claimed in claim 1 which is 1,3-di-(2,3-dihydroxypropyl)-4,5,6,7-tetrabromobenzimidazolone.
11. A compound as claimed in claim 1 which is 1,3-di-(2-hydroxyethyl)-5,6-dibromobenzimidazolone.
12. A compound as claimed in claim 1 which is 1,3-di-(2-hydroxyethyl)-5,6-dibromo-4,7-dichlorobenzimidazolone.
13. A compound as claimed in claim 1 which is 1,3-di-(2-hydroxyethyl)-5,6-dichlorobenzimidazolone.
14. A compound as claimed in claim 1 which is 1,3-di-(2-hydroxyethyl)-4,7-dibromo-5,6-dichlorobenzimidazolone.
15. A compound as claimed in claim 1 which is 1,3-di-(2-hydroxyethyl)-4,5,6-tribromobenzimidazolone.
16. A compound as claimed in claim 1 which is 1,3-di-(2-hydroxy-2-phenylethyl)-4,5,6,7-tetrabromobenzimidazolone.
17. A compound as claimed in claim 1 which is 1,3-di-(2-hydroxycyclohexyl)-5,6-dibromobenzimidazolone.
18. A compound as claimed in claim 1 which is 1,3-di-(γ-aminopropyl)-4,5,6,7-tetrabromobenzimidazolone.
19. A compound as claimed in claim 1 which is 1,3-di-(β-carboxyethyl)-4,5,6,7-tetrabromobenzimidazolone.
20. A compound as claimed in claim 1 which is 1,3-di-(carboxymethyl)-4,5,6,7-tetrabromobenzimidazolone.
21. A compound as claimed in claim 1 which is 1,3-di-(2-chloroethyl)-5,6-dibromobenzimidazolone.

* * * * *